US011406778B2

(12) United States Patent
D'Angelo et al.

(10) Patent No.: US 11,406,778 B2
(45) Date of Patent: *Aug. 9, 2022

(54) UNLOCKING A RESPIRATORY MODE

(71) Applicant: KONINKLIJKE PHILIPS N.V., Eindhoven (NL)

(72) Inventors: Mark D'Angelo, Monroeville, PA (US); John Raymond Pujol, Murrysville, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 251 days.

This patent is subject to a terminal disclaimer.

(21) Appl. No.: 16/791,399

(22) Filed: Feb. 14, 2020

(65) Prior Publication Data
US 2020/0179628 A1  Jun. 11, 2020

Related U.S. Application Data

(63) Continuation-in-part of application No. 14/125,663, filed on Dec. 12, 2013, now Pat. No. 10,576,223.
(Continued)

(51) Int. Cl.
*A61M 16/00* (2006.01)
*G16H 40/67* (2018.01)
(Continued)

(52) U.S. Cl.
CPC .......... *A61M 16/024* (2017.08); *G16H 20/30* (2018.01); *G16H 40/40* (2018.01); *G16H 40/67* (2018.01); *G16H 50/30* (2018.01); *G06F 3/0481* (2013.01)

(58) Field of Classification Search
CPC .. A61M 16/00; A61M 16/0051; A61M 16/10; A61M 2205/27; A61M 2205/276;
(Continued)

(56) References Cited

U.S. PATENT DOCUMENTS

| 10,576,223 B2 * | 3/2020 | D'Angelo ........... A61M 16/024 |
| 2002/0036601 A1 * | 3/2002 | Puckeridge ............ H01H 9/181 345/55 |

(Continued)

FOREIGN PATENT DOCUMENTS

| CN | 1736324 A | 2/2006 |
| WO | 0132069 A2 | 5/2001 |

(Continued)

*Primary Examiner* — Valerie L Woodward

(57) ABSTRACT

A system to configure respiratory therapy modes for users of respiratory therapy devices comprises one or more processors configured to execute computer program modules. The modules include a data gathering module for receiving usage information related to a respiratory therapy device in a first therapy mode, an analysis module for determining effectiveness information related to effectiveness of therapy, a provider interface module configured for receiving a first unlock selection based on the determined effectiveness information, the first unlock selection being received while the respiratory therapy device is operating in the first therapy mode, the first unlock selection indicating that a second therapy mode for the respiratory therapy device should be unlocked, and a device configuration module configured such that, responsive to reception of the first unlock selection by the provider interface module, the device configuration module activates the second therapy mode for the respiratory therapy device.

34 Claims, 7 Drawing Sheets

Related U.S. Application Data

(60) Provisional application No. 61/497,239, filed on Jun. 15, 2011.

(51) Int. Cl.
*G16H 40/40* (2018.01)
*G16H 50/30* (2018.01)
*G16H 20/30* (2018.01)
*G06F 3/0481* (2022.01)

(58) Field of Classification Search
CPC ...... A61M 2205/3553; A61M 2205/50; A61M 2205/005
See application file for complete search history.

(56) References Cited

U.S. PATENT DOCUMENTS

| | | |
|---|---|---|
| 2002/0077856 A1 | 6/2002 | Pawlikowski |
| 2005/0217674 A1 | 10/2005 | Burton |
| 2007/0000491 A1* | 1/2007 | Chalvignac .......... A61M 16/021 128/204.23 |
| 2007/0113849 A1 | 5/2007 | Matthews |
| 2007/0193583 A1* | 8/2007 | Reed .................... A61M 16/021 128/204.18 |
| 2009/0107498 A1 | 4/2009 | Plattner |
| 2010/0108064 A1* | 5/2010 | Blackwell ........... A61M 16/024 128/204.21 |
| 2010/0218766 A1* | 9/2010 | Milne ............... A61M 16/0063 128/204.23 |
| 2012/0291783 A1 | 11/2012 | Peiris |
| 2012/0304995 A1* | 12/2012 | Kauc ................. A61M 16/0051 128/204.23 |

FOREIGN PATENT DOCUMENTS

| | | |
|---|---|---|
| WO | 202009375 A1 | 9/2010 |
| WO | 2011004274 A1 | 1/2011 |
| WO | 2011021118 A1 | 2/2011 |

* cited by examiner

UNLOCKING A RESPIRATORY MODE

CROSS-REFERENCE TO RELATED APPLICATIONS

This patent application claims priority to U.S. application Ser. No. 14/125,663, filed on Dec. 12, 2013, which claims the priority benefit under 35 U.S.C. § 119(e) of U.S. Provisional Application No. 61/497,239 filed on Jun. 15, 2011, the contents of which are herein incorporated by reference.

BACKGROUND OF THE INVENTION

1. Field of the Invention

The present disclosure pertains to methods and systems to configure respiratory therapy modes in respiratory therapy devices.

2. Description of the Related Art

Treating respiratory disorders with pressure support therapy is known. In particular, the use of positive airway pressure (PAP) therapy is common. Some subjects may experience respiratory disturbances, despite adhering to e.g. a PAP therapy mode. In other words, a (prescribed) therapy mode may not be effective for all subjects. Today PAP therapy devices may support multiple modes, but the selection is determined by the clinician. While these modes can be applied readily to a single clinical condition, they have the deficiency of only providing a fixed specific clinical benefit. They also require a clinical practitioner's involvement in all steps of therapy from diagnosing and prescribing a therapy mode to making decisions for future applications of therapy.

SUMMARY OF THE INVENTION

One or more embodiments of the present disclosure relate to providing a system to configure respiratory therapy modes for users of respiratory therapy devices. The system comprises one or more processors configured to execute computer program modules. The computer program modules comprise a data gathering module configured to receive usage information related to a respiratory therapy device in a first therapy mode, wherein the usage information received from the respiratory therapy device represents therapeutic usage of the respiratory therapy device during the first therapy mode; an analysis module configured to determine effectiveness information related to effectiveness of therapy based on the usage information during the first therapy mode; a provider interface module configured to receive a first unlock selection based on the determined effectiveness information, the first unlock selection being received while the respiratory therapy device is operating in the first therapy mode, the first unlock selection indicating that a second therapy mode for the respiratory therapy device should be unlocked, wherein the second therapy mode is different than the first therapy mode, and the second therapy mode is not available for use on the respiratory therapy device prior to reception of the first unlock selection; and a device configuration module configured such that, responsive to reception of the first unlock selection by the provider interface module, the device configuration module activates the second therapy mode for the respiratory therapy device.

It is yet another aspect of the present disclosure one or more embodiments to provide a method to configure respiratory therapy modes for users of respiratory therapy devices. The method comprises receiving usage information related to a respiratory therapy device in a first therapy mode, wherein the received usage information represents therapeutic usage of the respiratory therapy device during the first therapy mode; determining effectiveness information related to effectiveness of therapy based on the usage information during the first therapy mode; receiving a first unlock selection based on the effectiveness information, the first unlock selection being received while the respiratory therapy device is operating in the first therapy mode, the first unlock selection indicating that a second therapy mode for the respiratory therapy device should be unlocked, wherein the second therapy mode is different than the first therapy mode, and the second therapy mode is not available for use on the respiratory therapy device prior to reception of the first unlock selection; and responsive to reception of the first unlock selection, activating the second therapy mode for the respiratory therapy device.

It is yet another aspect of the present disclosure one or more embodiments to provide a system for configuring respiratory therapy modes for users of respiratory therapy devices. The system comprises: means for receiving usage information related to a respiratory therapy device in a first therapy mode, wherein the received usage information represents therapeutic usage of the respiratory therapy device during the first therapy mode; means for determining effectiveness information related to effectiveness of therapy based on the usage information during the first therapy mode; means for receiving a first unlock selection based on the effectiveness information, the first unlock selection being received while the respiratory therapy device is operating in the first therapy mode, the first unlock selection indicating that a second therapy mode for the respiratory therapy device should be unlocked, wherein the second therapy mode is different than the first therapy mode, and the second therapy mode is not available for use on the respiratory therapy device prior to reception of the first unlock selection; and means for activating the second therapy mode for the respiratory therapy device, responsive to reception of the first unlock selection.

It is yet another aspect of the present disclosure, one or more embodiments to provide a computer-readable medium storing instructions that, when executed by a computer, cause it to: receive usage information related to a respiratory therapy device in a first therapy mode; determine effectiveness information related to effectiveness of therapy based on the usage information during the first therapy mode; and activate a second therapy mode based on the usage information during the first therapy mode, the second therapy mode being a multimode therapy.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of any limits.

DETAILED DESCRIPTION OF EXEMPLARY EMBODIMENTS

Figure 1:
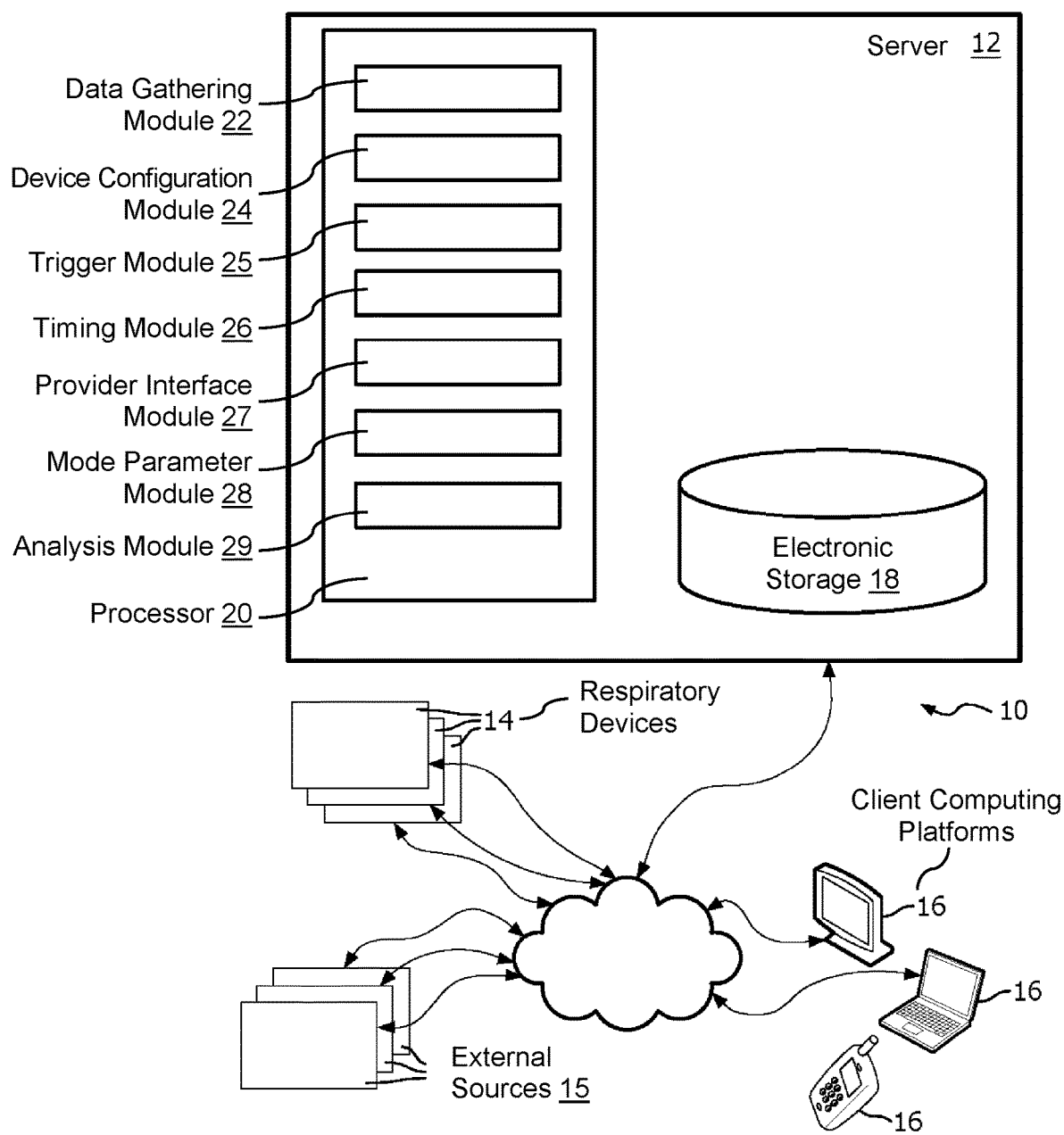
FIG. 1 schematically illustrates a system to configure respiratory therapy modes for users of respiratory therapy devices.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 10 to configure respiratory therapy modes for users of respiratory therapy devices 14. A respiratory therapy device 14 may connect to a server 12 to facilitate the exchange of information, including configuration commands. In some cases, adherence to a therapy regimen involving a respiratory therapy device 14 may be challenging for some subjects. Given a predetermined set of circumstances, commonly including, e.g., a measure representing insufficient effectiveness of, or adherence to, a first therapy mode, stability of the first therapy mode, a care provider may decide that a subject should use a second therapy mode that is different from the first therapy mode. The first therapy mode may be referred to as the original mode, the default mode, and/or the initial mode.

In general, each therapy mode can be applied readily to a single clinical condition. In some cases, the therapy modes have the deficiency of only providing a fixed clinical benefit. However, in some cases, PAP therapy may influence ventilation stability (e.g., CPAP therapy increases plant gain). An impact on ventilation stability as a result of pressure change (e.g., as a result of therapy mode change) may be determined based on how stable the patient is and how much the ventilation controller has been active. For example, in cases of titration therapy and/or changes in therapy modes, changes in in PAP pressure may contribute to instability. In a multimode PAP system, when the system makes a request for a change in pressure (e.g. increase), the impact to stability can be computed. If the patient is mostly stable and there is room left in the ventilation controller, then the requested change (e.g., full increase in CPAP pressure) can be tolerated. Otherwise, only some portion of the requested change (e.g., CPAP pressure increase) is permitted. This decision process may continue to process each of the change requests (from the PAP system) until all of the therapy modes (therapy subsystems) have been considered and are in agreement. A control arbitrator may be needed when new boundary conditions are met. The output from the fixed modes (fixed modality PAP therapy modes) is a list of therapy response signals that are then combined for the delivery of the multimode therapy.

A "mode" of a respiratory therapy device broadly defines the range of capabilities that the respiratory therapy device can perform. In some embodiments, the range of capabilities pertains to inhalation pressure levels and exhalation pressure levels, FE state, volume setpoints, peak flow setpoints, etc. Examples of therapy modes may include one or more of a CPAP mode; a multi-pressure mode (e.g., bi-level pressure or BIPAP); Average Volume Assured Pressure Support (AVAPS) mode; Proportional Assist Ventilation (PAV) mode; Auto Servo Ventilation (ASV) mode; Flow Based Gain Therapy (FBGT) mode; Loop Gain Therapy mode and/or other modes. Each of these modes are designed with specific therapeutic goals. In some cases, the pressure delivery is personalized to the individual (e.g., throughout a therapy session). Some therapy modes are capable of auto-titration, whereas other modes are not.

Definitions:

PAP Therapy: The basic positive airway pressure device contains a pneumatic source such as a rotating fan, a pressure sensor for closed loop fan control and pneumotachograph to measure airflow. The patient is connected by a flexible conduit and a mask with a deliberate orifice to allow for exhaust of CO2. Using the pressure sensor as feedback the fan speed is adjusted desired mask pressure which includes pressure drops for conduit and mask determined by current flow conditions. Small residual flow based control errors may affect patient loop gain as the mask pressure varies due to pressure control dynamics.

Loopgain: The formal diagnostic assessment of respiratory loopgain is well established in the clinical community. Some of those methods involve conducting laboratory tests, while other less invasive methods have been described using information from PSG. In CSA and treatment emergent periodic breathing loopgain patients exhibit a cyclic respiratory pattern which mathematically is described well in frequency domain mathematics. In OSA, the over ventilation response to an obstructive event requires different analysis methods. For the description in this disclosure, recognizing there will not be a single form of representation, the term loopgain will be used as a general term, non-specific to any specific algorithm or method of loopgain determination. For this discussion, loopgain may be any form of descriptive representation of ventilation stability including but not limited to existing known published forms of loopgain, time constants of response, rate of change metrics, flow rate, overshoot measurements, sleep stage, arousals, etc. Additionally, loopgain may be represented as a composite metric. Chemosensitivity in CSA patients: For CSA and treatment emergent periodic breathing, during waxing and waning breathing patterns, a gain scheduler proportional to the magnitude and/or rate of change of the waxing and waning pattern would make additions to or reductions from patient effort thus acting in equal to and opposition to the astable muscle efforts of the patient. In doing so, this therapy provides more normalized ventilation and entrains the central controller into a stable breathing pattern.

Chemosensitivity in OSA patients: Obstructed sleep apnea patients with chemosensitivity will also benefit from this therapy. During obstructive events, as a result of an arousal response to hypoxemia, large swings in ventilation occur. This therapy provides a similar benefit to the patient using flow based gain scheduling. In this case, most events are prevented by not allowing muscle effort to cause swings in minute ventilation sufficient to allow this pattern to begin.

Table 1 lists some examples of typical fixed modality PAP therapies:

and prescribes a set of therapy control outputs (therapy mode parameters) for the next time period. The therapy control outputs are typically configuration commands that dictate one or more mode parameters for a therapy mode of the device. In some embodiments, mode parameters may affect the operation of respiratory therapy device 14 in a particular therapy mode in a persistent manner, i.e. for more than one respiratory cycle. Examples of therapy mode parameters may include inspiratory pressure, expiratory pressure, I/E state, volume setpoints, peak flow setpoints, and/or other parameters that affect the operation of respiratory therapy device 14 whilst in a particular therapy mode. In some embodiments, each of these fixed modes (fixed modality PAP therapy modes) generate the therapy control outputs (therapy mode parameters) within a range of values. For example, an auto CPAP algorithm is given a range of EPAPmin pressures, a range of EPAPmax values to operate within, receives inputs such as I/E state, SDB events, snoring and makes pressure recommendations for mask

TABLE 1

Continuous Positive Airway Pressure CPAP, primarily used for obstructive sleep apnea, but also used in acute cardiogenic pulmonary edema.
BiLevel Pressure or BiPAP, alternating high and low pressure to drive ventilation during inspiration. This mode is primarily used in patients with resistive, restrictive lung disease and obesity hypoventilation patients. BiPAP delivers consistent pressure support regardless of patient effort. The resulting tidal volumes will vary, and depending on the amount of pressure support configured, the patient may be left with no control in the inspired tidal volume. This can be destabilizing to high loop gain patients, and is likely to cause hypocapnea. BiPAP can be configured to deliver machine initiated or timed breaths when patient effort is absent or reduced due to hypocapnea.
Average Volume Assured Pressure Support or AVAPS, this mode uses the benefits of BiPAP with a closed loop control around a tidal volume setpoint. This mode is beneficial to BiPAP patients with the added benefit of downregulating pressure support in accordance with patient muscle effort. AVAPS can also support machine breaths.
PAV, Proportional Assist Ventilation: This mode is implemented by monitoring the instantaneous patient flow rate $\dot{V}$ and volume (V) and computes ab applied pressure (P) according to the equation of motion $[P = f1(V) + f2(\dot{V})]$, where f1 and f2 are appropriately selected functions for the relation between pressure and volume (elastic assist) and pressure and flow (resistive assist). "Proportional Assist Ventilation, a New Approach to Ventilatory Support" https://doi.org/10.1164/ajrccm/145.1.114
Auto Servo Ventilation ASV, this mode is designed to treat patients with high loop gain ventilation control deficiencies. The device monitors some aspect of ventilation and provides pressure support only as needed to maintain some proportion of that value (typically 90% of monitored value). Because of that proportion, the design allows the patient to guide the therapy. Similar to BiPAP, machine breaths can be configured in this mode.
Flow Based Gain Therapy, FBGT: a general term that may incorporate one or combination of specific means to alter device pap therapy interaction with the patient. As discussed in WO 2011/086435 SERVO VENTILATION USING NEGATIVE PRESSURE SUPPORT and WO 2011/086434 SERVO VENTILATION USING PRESSURE DROP FROM BASELINE, it is possible to oppose muscle effort and reduce the effective ventilation in a patient utilizing negative pressure support. For the present disclosure, we shall envision a flow based gain capability by which a portion of the supported mask pressure is computed as a gain factor multiplied by the instantaneous patient flow rate. The gain factor, when positive, would drive ventilation, and when negative, would restrict ventilation. While the application of a patient flow based gain may appear similar to the PAV equation, there are clear differences in intent. PAV incorporates a flow based gain factor to overcome respiratory impedance. In this therapy, the flow based gain is altered to manage ventilation stability. Including the application of negative gain to counteract muscle effort. Flow based ventilation gain therapy acts as a control stabilizer for the central controller.
Loop Gain Therapy: For chemosensitivity and high loop gain patients, this therapy algorithm provides targeted pap therapy intervention designed to abate unstable loop gain based breathing disorders.

In general, in some embodiments, the operating construct for these modes may be as follows: On a continuous-time basis a set of therapy response signals (e.g., usage information described below) are delivered to an algorithm. The algorithm processes the data based on its targeted outcomes pressure continuously throughout the night. In some cases, the range of values is a predetermined range of values (e.g., determined by a clinician). In other cases, the range of values is determined dynamically (e.g., based on the usage information described below).

Table 2 illustrates how each of these fixed modalities has been designed for a particular disease state using a variety of control metrics:

| ID | Sub Therapy | Abbreviation | Disease State | Control Metric | Breathing Phase |
|---|---|---|---|---|---|
| 1 | Flow Based Gain Therapy | FBGT | Ventilation Instability | Flow based pressure augmentation | Throughout |
| 2 | Automatic Continuous Positive Airway Pressure | Auto CPAP | Obstructed Sleep Apnea | Expiration Pressure | Throughout |
| 3 | Auto Servo Ventilation | ASV | Periodic breathing | Expiratory Pressure, Pressure Support | Expiration (ASVe) Inspiration (ASVi) |
| 4 | Average Volume Assured Ventilation | AVAPS | Lung disease, obesity hypoventilation syndrome | PS minimum | Inspiration |
| 5 | Flex | Cflex, BiFlex | comfort | Flow based pressure augmentation | Expiration |
| 6 | Airflow Comfort | AC | comfort | Flow based pressure augmentation | Throughout |
| 7 | Otis Work of Breathing | Otis | comfort | Pressure Support For Work Of breathing | Inspiration |

In some embodiments, system 10 may include one or more servers 12, respiratory devices 14, and/or other components. System 10 may operate in communication and/or coordination with one or more external sources 15. Users, including care providers, may interface with system 10 and/or respiratory therapy devices 14 via client computing platforms 16. The components of system 10, servers 12, respiratory therapy devices 14, and/or client computing platforms 16 may be operatively linked via one or more electronic communication links. For example, such electronic communication links may be established, at least in part, via one or more networks such as the Internet and/or other networks. It will be appreciated that this is not intended to be limiting, and that the scope of this disclosure includes implementations in which servers 12, respiratory therapy devices 14, and/or client computing platforms 16 may be operatively linked via some other communication media. The components of system 10 may be integrated into fewer or more devices than shown in FIG. 1. The described functionality of the components of system 10 may be distributed across partitions different from the one shown in FIG. 1. For example, the user interface for a care provider may be integrated into a respiratory therapy device.

As is discussed further below with respect to FIG. 2, respiratory therapy devices 14 are capable of configuration in accordance with one or more embodiments. The respiratory therapy devices may be configured locally (using a UI, smart card, and/or other local technique, device, or process, for configuration, or combination thereof), or remotely (using one or more networks, and/or other remote technique, device, or process, for configuration or combination thereof), and/or both. Configuration may be under control of (automated) programming, or may be under control of a care provider, and/or a combination of both.

A given respiratory therapy device 14 is configured to provide respiratory therapy through the supply of a pressurized flow of breathable gas to a subject in accordance with a therapeutic respiratory regimen. Respiratory therapy may be delivered in different therapy modes. A therapy device manufacturer, distributor, and/or operator may have different compensation requirements, or costs, for subjects. For example, the cost of a given PAP therapy mode may be less than other types of pressure support therapy. The cost assigned to a therapy mode may be a function of therapy stability, sophistication, comfort, effectiveness, efficiency, and/or other parameters. In some embodiments, configuration of respiratory therapy devices 14 that are capable of providing different modes of respiratory therapy may provide an efficient procedure for testing respiratory therapies (in terms of stability, effectiveness, comfort, and/or other usage parameters) for individual subjects.

A given client computing platform 16 may include one or more processors configured to execute computer program modules. The computer program modules may be configured to enable one or more users (e.g. care providers) associated with the given client computing platform 16 to interface with system 10 and/or respiratory therapy devices 14, and/or provide other functionality attributed herein to client computing platforms 16. By way of non-limiting example, the given client computing platform 16 may include one or more of a desktop computer, a laptop computer, a handheld computer, a NetBook, a Smartphone, a gaming console, a wearable device, and/or other computing platforms. Alternatively, and/or simultaneously, a given client computing platform 16 may be integrated in or embedded in a user's respiratory therapy device 14.

External resources 15 may include sources of information, external entities participating with system 10, therapeutic devices, and/or other resources. In some implementations, some or all of the functionality attributed herein to external resources 15 may be provided by resources included in system 10.

Server 12 may configure, or cooperate with client computing platforms 16 to configure, one or more respiratory therapy modes for users of respiratory therapy devices 14. Server 12 may include electronic storage 18, one or more processors 20, and/or other components. Server 12 may include communication lines, or ports to enable the exchange of information with one or more networks and/or other computing platforms.

Electronic storage 18 may comprise electronic storage media that electronically stores information. The electronic storage media of electronic storage 18 may include one or both of system storage that is provided integrally (i.e., substantially non-removable) with server 12 and/or removable storage that is removably connectable to server 12 via, for example, a port (e.g., a USB port, a FireWire port, etc.) or a drive (e.g., a disk drive, etc.). Electronic storage 18 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 18 may store software algorithms, information determined by processor 20, information obtained, identified, gathered, and/or provided by one or more computer program modules, information received from server 12, information received from client computing platforms 16, information received from respiratory therapy devices 14, and/or other information that enables server 12 to function properly.

Processor(s) 20 is configured to provide information processing capabilities in server 12. As such, processor 20 may include one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may include a plurality of processing units. These processing units may be physically located within the same device, or processor 20 may represent processing functionality of a plurality of devices operating in coordination.

As is shown in FIG. 1, processor 20 may be configured to execute one or more computer program modules. The one or more computer program modules may include one or more of a data gathering module 22, a device configuration module 24, a trigger module 25, a timing module 26, a provider interface module 27, a mode parameter module 28, an analysis module 29, and/or other modules. Processor 20 may be configured to execute modules 22, 24, 25, 26, 27, 28, and/or 29 by software; hardware; firmware; some combination of software, hardware, and/or firmware; and/or other mechanisms for configuring processing capabilities on processor 20.

It should be appreciated that although modules 22, 24, 25, 26, 27, 28, and 29 are illustrated in FIG. 1 as being co-located within a single processing unit, in implementations in which processor 20 includes multiple processing units, one or more of modules 22, 24, 25, 26, 27, 28, and/or 29 may be located remotely from the other modules. The description of the functionality provided by the different modules 22, 24, 25, 26, 27, 28, and/or 29 described below is for illustrative purposes, and is not intended to be limiting, as any of modules 22, 24, 25, 26, 27, 28, and/or 29 may provide more or less functionality than is described. For example, one or more of modules 22, 24, 25, 26, 27, 28, and/or 29 may be eliminated, and some or all of its functionality may be provided by other ones of modules 22, 24, 25, 26, 27, 28, and/or 29. As another example, processor 20 may be configured to execute one or more additional modules that may perform some or all of the functionality attributed below to one of modules 22, 24, 25, 26, 27, 28, and/or 29.

It will be appreciated that the illustration of modules 22, 24, 25, 26, 27, 28, and/or 29 being executed solely on processor 20 separate from client computing platforms 16 and respiratory therapy devices 14 is not intended to be limiting. For example, in some implementations, the client computing platforms 16 may be configured to provide locally at least some of the functionality attributed above to one or more of modules 22, 24, 25, 26, 27, 28, and/or 29. Similarly, one or more of modules 22, 24, 25, 26, 27, 28, and/or 29 may be executed locally on individual client computing platforms 16 while others are executed on server 12. As another example, in some implementations, the respiratory therapy devices 14 may be configured to provide locally at least some of the functionality attributed above to one or more of modules 22, 24, 25, 26, 27, 28, and/or 29. Similarly, one or more of modules 22, 24, 25, 26, 27, 28, and/or 29 may be executed locally on individual respiratory therapy devices 14 while others, if present, may be executed remotely from individual respiratory therapy devices 14.

Data gathering module 22 is configured to receive usage information related to one or more respiratory therapy devices 14. Receiving usage information may include receiving transmission from one or both of a given respiratory therapy device 14 and/or a given client computing platform 16. Usage information may refer to any type of monitored data during usage of the respiratory therapy device. In some embodiments, the received usage information represents therapeutic usage of the given device in its current therapy mode, i.e. the therapy mode that is currently active. For example, a given respiratory therapy device 14 may operate in a PAP therapy mode (e.g., CPAP mode, or any other therapy mode) and transmit in real-time, near real-time, hourly, daily, weekly, monthly, annually, or on demand usage information, and/or usage information for any period of time. In some embodiments, the usage information may include the total hours of cumulative therapeutic usage during a previous time period (e.g., in hours, days, weeks, months, or years), and/or during a single or multiple therapy sessions. Usage information may be associated with either a particular respiratory therapy device 14, a particular subject, and/or both.

Usage information, in some embodiments, may include one or more subject respiratory parameters related to the current therapy mode. For example, in some embodiments, the subject respiratory parameters for the current therapy mode may be as few as a single parameter (input) such as flow from the therapy device. In other modes, the subject respiratory parameters (input) may include breath rate, tidal volume, peak flow, minute ventilation, presence of snoring, periodic breathing, etc. In some embodiments, these monitored subject respiratory parameters (inputs) may be used to derive treatment targets (e.g., the ASV device calculates a peak flow target as a function of monitored peak flow values). In some embodiments, usage information (e.g., monitored data) may include information/data outside of the pap such as heart signals, brain signals, blood pressure, body weight, etc.

In some embodiments, usage information includes features that may be used to determine respiratory stability. For example, such features may include one or more of rate of change of minute ventilation, ventilation overshoot detection, ventilation undershoot detection, period, phase, and amplitude of periodic breathing, average minute ventilation, $CO_2$ consumption, sleep stage, arousal of central nervous system, and/or other respiratory or physiological features.

Usage information, in some embodiments, may include one or more of a therapy starting date, user experience level, an average duration of daily usage, a usage pattern, metrics indicating quality of therapy and/or quality of sleep, level of compliance with a therapy regimen, therapeutic device characteristics (e.g. mask type or settings of respiratory therapy device 14), derived usage characteristics, user-stated usage characteristics, and/or other usage information. User-stated usage characteristics may include issues or problems the user is experiencing while undergoing therapy, and/or other user-stated usage characteristics. Derived usage characteristics may include low and/or irregular usage (as detected e.g. through analysis of usage reports), decreasing average daily usage, excessive mask leak, and/or other derived usage characteristics. Respiratory therapy device 14 may (autonomously and/or periodically) compile a usage report and submit it to server 12.

Timing module 26 may be configured to determine whether a threshold amount of therapeutic usage time (and/or calendar time) has elapsed for one or more respiratory therapy devices 14. For a given device, a threshold amount of time may include one or both of a cumulative usage threshold and/or a consecutive usage threshold. For example, in some embodiments, system 10 may be configured to switch from one therapy mode to another therapy mode only after at least a predetermined amount of time (e.g., number of hours, days, weeks, and/or any predetermined amount of time) of therapeutic usage have occurred, and/or at least a predetermined amount of time (e.g., number of hours, days, weeks, and/or any predetermined amount of time) of consecutive therapeutic usage have occurred. Alternatively, and/or simultaneously, timing module 26 may be configured to determine whether a trial period (e.g. for a trial therapy mode) has expired. A trial period may be specified in calendar time (e.g., hours, days, weeks, months, etc.), usage time (e.g., cumulative usage and/or consecutive usage in hours, days, weeks, months, etc.), and/or other time-based metrics, and/or any combination thereof. In some embodiments, operation of constituent components of system 10, e.g. device configuration module 24 and/or data gathering module 22, may be responsive to a determination by timing module 26.

In some embodiments, timing module 26 may be configured to cooperate with a timing module internal to a given respiratory therapy device 14. For example, once a trial mode of therapy is activated in a given respiratory therapy device 14, the determination that the trial period has expired may be made independently by a given respiratory therapy device 14, without requiring the respiratory therapy device 14 to interact with system 10 or a network (e.g. the Encore-Anywhere network).

Analysis module 29, in some embodiments, may be configured to analyze information received from usage information module and/or timing module. For example, analysis module may be configured to determine therapy stability, comfort, effectiveness, efficiency, and/or other parameters related to a given therapy mode (e.g., fixed modality therapy mode, and/or multimode therapy). The therapy mode(e.g., fixed modality therapy mode, and/or multimode therapy), may be the current therapy mode, or the mode being considered for therapy (e.g., second, third mode, etc.) In some embodiments, analysis module 29 may be configured to determine stability based on one or more of rate of change of minute ventilation, ventilation overshoot detection, ventilation undershoot detection, period, phase, and amplitude of periodic breathing, average minute ventilation, $CO_2$ consumption, sleep stage, arousal of central nervous system, and/or other respiratory or physiological features.

In some embodiments, analysis module 29 may be configured determine a respiratory disturbance index (RDI), a sleep quality index, and/or other indexes or information related to the effectiveness and/or efficiency of the therapy provided by respiratory therapy device 14. The index(es) and/or information may be determined by analysis module 29 based on received usage information. Analysis module 29 may be configured to determine the RDI by adding together the number of apneas, the number of hypopneas, and the number of respiratory effort related arousals (RERAs) in a given time period. RDI may be interpreted as a measure for the efficiency of a particular respiratory therapy. A determination made by analysis module 29 may be used in other constituent components of system 10, e.g. trigger module 25.

Trigger module 25 may be configured to determine whether a trigger event occurred pertaining to a given respiratory therapy device 14, its user, and/or both. For example, a trigger event may include detection that a subject is experiencing many respiratory disturbances in spite of undergoing respiratory therapy, receiving notification from respiratory therapy device 14 that a subject is experiencing many respiratory disturbances in spite of undergoing respiratory therapy, determinations based on received usage information, instructions and/or commands received from a care provider, and/or other events. An occurrence of a trigger event may include one or more conditions that need to be satisfied simultaneously and/or consecutively. For example, a trigger event may include a usage time threshold (e.g. determined by timing module 26), and/or a usage information threshold.

A trigger event may be based on operation of analysis module 29, which may determine (autonomously, without explicit intervention from a care provider and/or a user) that the current therapy mode is not stable, not sufficiently effective and/or efficient. In some embodiments, a trigger event may be detected based on one or more monitored data (e.g., usage information) reaching a threshold value. The threshold may be a predetermined threshold, may be set based on a per-user basis, may be set manually by a caregiver, and/or determined in other ways.

In some implementations, trigger module 25 is configured to detect a trigger event responsive to RDI (and/or some other index or parameter) determined by analysis module 29 crossing a threshold. The threshold may be a predetermined threshold, may be set based on a per-user basis, may be set manually by a caregiver, and/or determined in other ways. In some implementations, trigger module 25 is configured to detect a trigger event responsive to a minimum amount of usage time per day for a predetermined number of consecutive days. This predetermined number may be any number between 2 and 20. The occurrence of a trigger event may be used by other constituent components of system 10 to perform a particular predetermined action.

Trigger module 25 may take into account whether a subject has undergone a particular mode of respiratory therapy using more than one mask. In some embodiments, a therapy mode should not be unlocked unless a predetermined number of different masks have been used by the subject, e.g. for a threshold amount of time. Logical combinations of basic trigger events to form more complex trigger events are contemplated.

Trigger module 25 may be configured to allow a care provider to manually override the determination whether a trigger event occurred. Alternatively, and/or simultaneously, a care provider may be able to override (remotely) any operational settings, including therapy mode and parameters, for any of the respiratory therapy devices 14.

Mode parameter module 28 may be configured to determine parameters of a therapy mode (as explained above, the therapy mode may be a fixed modality therapy, or a multi-mode therapy). In some embodiments, the parameters of a therapy mode may include, but not limited to, one or more pressure levels, a respiratory rate, a tidal volume, and/or other parameters. Mode parameter module 28 may provide one or more recommended parameters of a particular respiratory therapy, such as one or more pressure levels, to be included in the commands from device configuration module 24 to a given respiratory therapy device 14. Mode parameter module 28 may be configured to automatically update target parameters and/or recommended parameters for a therapy mode based on information gathered during therapeutic usage of respiratory therapy device 14.

In some embodiments, mode parameter module 28 may include a decision system configured to determine one or more mode (or multimode) therapy parameters. In some embodiments, the decision system is configured to compare the impact of change requests in a multimode therapy design. In some embodiments, the inputs to the decision system include the current monitored data (usage information) and the change request from each of the fixed therapy modes. In some embodiments, the decision process involves comparing the current monitored data and the impact that each change request will have on each adjacent therapy. In some embodiments, the decision process relies on a set of relationships between pressure delivery and typical ventilation responses. In some embodiments, this response data may begin as population based information but as therapy is delivered the information is updated per the patient's response. For example, the decision system may determine multimode therapy parameters on a response from one or more fixed therapy modes by sending therapy response signals into an algorithm and collecting the therapy control outputs from each of the modes. The decision system examines the therapy control outputs collectively to determine an optimal response. In some embodiments, once the decision system has determined the best combined therapy control outputs, this instruction set is used to determine the multimode therapy parameters.

In some embodiments, the decision system may be generated using machine learning methods to generate a comprehensive model using a multivariate approach with ventilation metrics. These ventilation metrics could be common respiratory parameters such as tidal volumes, minute ventilation, sleep disordered breathing events, etc. In some embodiments the ventilation metrics may could include time windowing, statistical processing for min, max, standard deviation. In machine learning models a single target is considered the dependent variable on the y axis or ordinate, and a multitude of independent variables/features can reside on the x axis or abscissa. The benefit of this approach is that the machine learning model may be computationally inexpensive relative to the target computation. The multivariate result may also be more generalized across populations and circumstances. Machine learning techniques include multi regression, linear, and neural networks. In some embodiments, the decision system may be generated using one or more methods in combination including rules based system, machine learning or neural network.

In some embodiments, the mode parameter module 28 (decision system) evaluates potential residuals of each of the therapy modes (treatments). This could include PAP treatments as well as other interventions (e.g., blood pressure medicine, or other treatments). Changes to therapy are targeted to provide benefit, and the potential residuals of that change in therapy are evaluated prior to introducing the change. Often the residuals may influence other physiological parameters. There may be second and third tier decisions to consider. For example, there are pros and cons of providing CPAP pressure for OSA. The pros include treating the OSA component. The cons may include increasing loop gain and causing respiratory instability. Here, regardless of the implementation, if the auto CPAP therapy is calling for an increase in CPAP pressure for obstructed events, that pressure increase may impact the stability of ventilation and needs to be validated by the decision system. If the patient's ventilation is stable, then the pressure increase is permitted to occur. Otherwise a tradeoff decision has to be made between potential risk and benefit of increasing CPAP pressure.

Evaluating a single change was illustrated in the example above, but there could be multiple changes, each with multiple tiers of residuals. Complex modeling can be used to model these interactions and adjusted for a particular patient. These complex models can be made using machine learning and neural nets.

Device configuration module 24 is configured to interact with respiratory therapy devices 14 to adjust operation of respiratory therapy devices 14. This includes adjusting one or more of a therapy mode, one or more parameters of a therapy mode, and/or other aspects/features of the operation of respiratory therapy devices 14. In some embodiments, responsive to reception of an unlock selection through provider interface module 27, device configuration module 24 activates a subsequent therapy mode. In some embodiments, device configuration module 27 deactivates the second therapy mode. For example, after a predetermined time period, after a trial period, and/or when a subsequent unlock selection is received.

For the purpose of this disclosure, "unlocking" a therapy mode may mean "making available for use and/or selection," "download instructions that implement said therapy mode," and/or other ways to enable a therapy mode on a respiratory therapy device that prior to the enablement was not available for use and/or selection. In some embodiments, activation and/or deactivation may require user interaction, or it may happen automatically without requiring user interaction. The unlocked second therapy mode may be a premium therapy mode, such as bi-level, auto-titration, a multi-pressure mode; Average Volume Assured Pressure Support (AVAPS) mode; Proportional Assist Ventilation (PAV) mode; Auto Servo Ventilation (ASV) mode; Flow Based Gain Therapy (FBGT) mode; Loop Gain Therapy mode, and/or other premium therapy modes. The unlocked second therapy mode may be a fixed modality therapy, and/or a multimode therapy.

For example, in some embodiments, in operation a clinician suspects a patient may benefit from an automatic form of therapy. The patient is connected to the multimode device and begins to breath on the device for baseline assessment. The device monitors data for a short period and recognizes obstructive sleep apnea events as well as ventilation control instability. The multimode device will solicit a response from one or more fixed therapy modes (fixed modality PAP therapy modes) by sending therapy response signals into the decision system (algorithm) and collects the therapy control outputs from each of the modes. The decision system examines the therapy control outputs collectively to determine an optimal response. In some cases, the decision device examines the therapy control outputs and optionally the therapy response signals to determine a response.

In our example above (providing CPAP pressure for treating OSA), CPAP pressure influences ventilation stability by increasing plant gain. The relationship between the increase in CPAP pressure and its contribution to stability is maintained by the system. When the CPAP system makes the request for an increase, the impact to stability is computed. The application of CPAP increases plant gain and the FBGT acts as a control stabilizer. Because the over titration of CPAP pressure introduces excessive plant gain and may introduce instability, the control decisions need to examine pros/cons within each target of the Multimode system. Once the decision system has determined the best combined therapy control outputs, this instruction set is used to drive the therapy for the next therapy session (e.g., the decision system applies a combination of auto CPAP therapy for the elimination of obstructive OSA events and FBGT to manage hyper chemosenstivity).

In some embodiments, delivery of multimode therapy is additive. The base PAP therapy from Table 2 may influence the directed pressure at the mask. Additionally, the FBGT will also influence the pressure directed towards the mask. Each of these is additive. For example, a base EPAP could be 10 cmH2O and during inspiration the FBGT could be instructing a 0.01 cmH2O/1 pm pressure augmentation. Each of these would be added for a net setpoint at the mask. The Multimode therapy design may call for an alteration of therapy outside the device, such as a change to a medication.

In some embodiments, pressure requests from each of the fixed modes (fixed modality PAP therapy modes) are combined for pressure delivery. Table 2 above, contains the therapy modes (subsystems) and the phase of breathing that each therapy mode (subsystem) interacts with. The pressure computation of each of these subsystems is independent from the others, some values are relevant only during expiration, others valid only during inspiration and some throughout the breath. In most cases, the pressure requests are independent from each of the other systems and combining them occurs without incidence. During inspiration we see the maximum pressure support request will be selected for that breath. The formulas below demonstrate how the pressures requests are combined for each phase of breathing.

During expiration:

Mask pressure=(Auto CPAP(2) or ASVe(3))+Flex(5)+FBGT(1)+AC(6)

During Inspiration:

Mask Pressure=(Auto CPAP(2) or ASV(3))+(maximum(AVAPS(4) or ASVi(3) or OTIS(7)))+FBGT(1)+AC(6)

Mode parameter module 28 may determine one or more mode parameters for the activated second, third therapy mode, or subsequent modes based on usage information received by data gathering module 22 during the original therapy mode. Device configuration module 24 may further dictate one or more determined mode parameters of the second or third therapy mode for the given device. The (transmitted) command may further dictate the period and/or condition after which the unlocked second or third therapy mode should be deactivated. For example, an unlocked and activated multi-pressure level therapy mode may expire after a trial period of 60 calendar days.

In some embodiments, device configuration module 24 may (re)activate the original therapy mode after expiration of a trial period of the second, the third, or subsequent therapy mode. Mode parameter module 28 may determine one or more updated mode parameters for the (re)activated original therapy mode based on usage information received by data gathering module 22 during any (combination) of preceding therapy modes. The (transmitted) command to (re)activate the original therapy mode may further dictate one or more determined updated mode parameters for the (re)activated original therapy mode for the given device.

As noted above, device configuration module 24 may activate a third therapy mode after expiration of a trial/usage period of the second therapy mode, such that the third therapy mode is different from the second therapy mode, as well as the original therapy mode. Mode parameter module 28 may determine one or more updated mode parameters for the newly activated third therapy mode based on usage information received by data gathering module 22 during any (combination) of preceding therapy modes. The (transmitted) command to activate the third therapy mode may further dictate one or more determined updated mode parameters for the third therapy mode for the given device. For example, the original, second, and third therapy modes may include CPAP therapy, bi-level therapy, and auto-titrating (e.g. AutoCPAP), respectively.

Device configuration module 24 may be configured to respond to the determination that a trigger event occurred. For example, a trigger event may be the determination that the current mode of respiratory therapy is not stable, and/or not sufficiently effective to treat a particular type of respiratory disorder for a given subject. In response to this determination, device configuration module 24 may, e.g. in conjunction with provider interface module 27 and/or mode parameter module 28, unlock and/or activate a second or third mode of respiratory therapy for the respiratory therapy device 14 associated with the given subject.

Provider interface module 27 is configured to receive a first unlock selection from a given care provider while the respiratory therapy device 14 is set on the first therapy mode. The first unlock selection may indicate that a second therapy mode should be unlocked. Through the generated user interface, a given care provider is able to unlock one or more therapy modes for individual respiratory therapy devices 14. The generated user interface is configured to present information to a caregiver and/or receive selection/entries from the caregiver that enable the caregiver to manage (remotely and/or locally) the therapy a subject receives from an individual respiratory therapy device 14. Such information and/or selections may include a subject identification, a respiratory therapy device identification, a therapy mode identifier, a therapy selection, trigger information, usage information, and/or other information, as well as other selections. In some embodiments, a selectable acceptance field may be activated, e.g., responsive to reception of the first unlock selection, wherein user selection of the selectable acceptance field indicates acceptance of the second therapy mode.

Responsive to such user selection of the selectable acceptance field, provider interface module 27 (or another constituent component of system 10) may cause device configuration module 24 to activate the second or third therapy mode. The described functionality may thus "unlock" a therapy mode responsive to the trigger event and selection by the caregiver. The (transmitted) command may result in automatic initiation of operating respiratory therapy device 14 in the second therapy mode. The (transmitted) command may result in other actions or operations by respiratory therapy device 14 that facilitate provision of pressure therapy in the second therapy mode to the subject.

Provider interface module 27 may be configured to respond to the determination that a trigger event occurred. For example, presenting a first or second or subsequent unlock selection to a care provider (and/or receiving a first or second or subsequent unlock selection from a care provider) may be responsive to the determination that a trigger event occurred.

Figure 3:
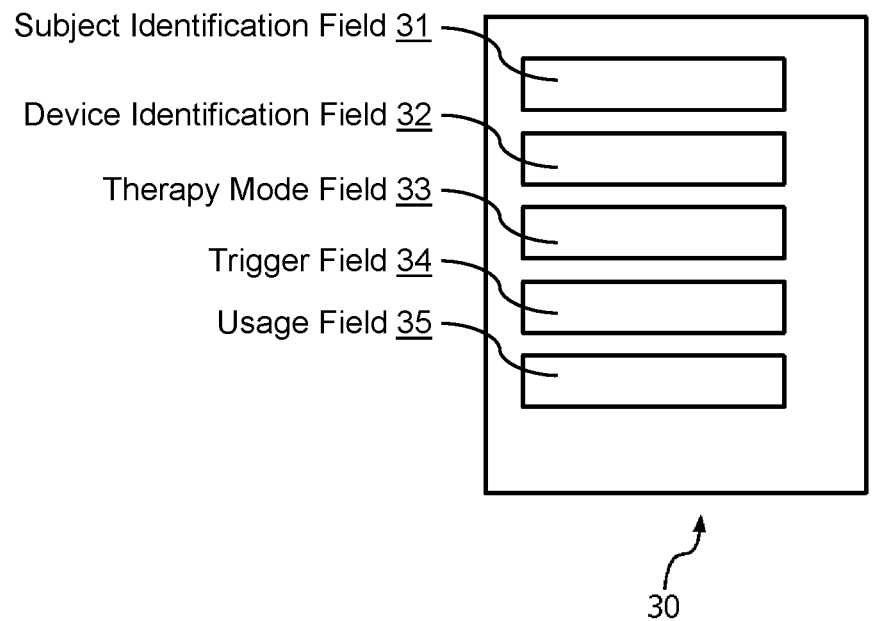
FIG. 3 illustrates an exemplary embodiment of a user interface, according to one or more embodiments.

By way of illustration, FIG. 3 illustrates an exemplary embodiment of a user interface 30 presented by provider interface module 27, e.g. through a client computing platform 16, according to one or more embodiments. A care provider may use a given client computing platform 16 to interact with system 10 and provider interface module 27. User interface 30 may include one or more fields configured to receive entry and/or selection of information pertaining to operational parameters and/or conditions of a given respiratory therapy device 14. Field 31 may be a subject identification field configured to present an identifier of the current subject associated with a given respiratory therapy device 14. Field 32 may be a device identification field configured to present an identifier of the given respiratory therapy device 14. Field 33 may be a therapy mode/unlock field configured to present the current therapy mode (and/or any of the parameters/settings associated with the current therapy mode) for a given respiratory therapy device 14. Field 33 may, optionally responsive to the occurrence of a trigger event, present a first or second or subsequent unlock selection, e.g., labeled with an identifier and/or representation of a second/third or other therapy mode that is different from the current therapy mode.

Selecting the first unlock selection may activate the second therapy mode for a given respiratory therapy device 14 (either indefinitely or for a trial period). Unlocking a second therapy mode may mean presenting the user of the given respiratory therapy device 14 with a selectable acceptance field (e.g. in a user interface of the given respiratory therapy device) to activate, upon selection, the unlocked second therapy mode. Field 34 may be a trigger field configured to present information pertaining to the occurrence of trigger events. For example, field 34 may present information pertaining to the determined, measured, estimated, and/or approximated effectiveness of the current therapy mode. Field 35 may be a usage field configured to present usage information to a user. For example, field 35 may present the average number of hours of nightly usage of a given respiratory therapy device 14.

Referring back to FIG. 1, in some embodiments, trigger module 25 is configured to determine whether a time-out trigger event occurred, pertaining to a given respiratory therapy device 14, its user, and/or both. Occurrence of a time-out trigger event may be based on one or more of a cumulative usage threshold, a consecutive usage threshold, a number of usage days, a number of calendar days, a target date, and/or other predetermined periods and/or thresholds. Responsive to the occurrence of a time-out trigger event (e.g. expiration of a predetermined trial period), device configuration module 24 may deactivate the previously unlocked (second/third) therapy mode. As a result, the respiratory therapy device 14 can no longer operate using the second/third therapy mode. Instead, operation of the respiratory therapy device 14 reverts to the therapy mode that was active prior to activating the unlocked second therapy mode, a.k.a. the original therapy mode or may revert to another, as yet not used, therapy mode.

Figure 2:
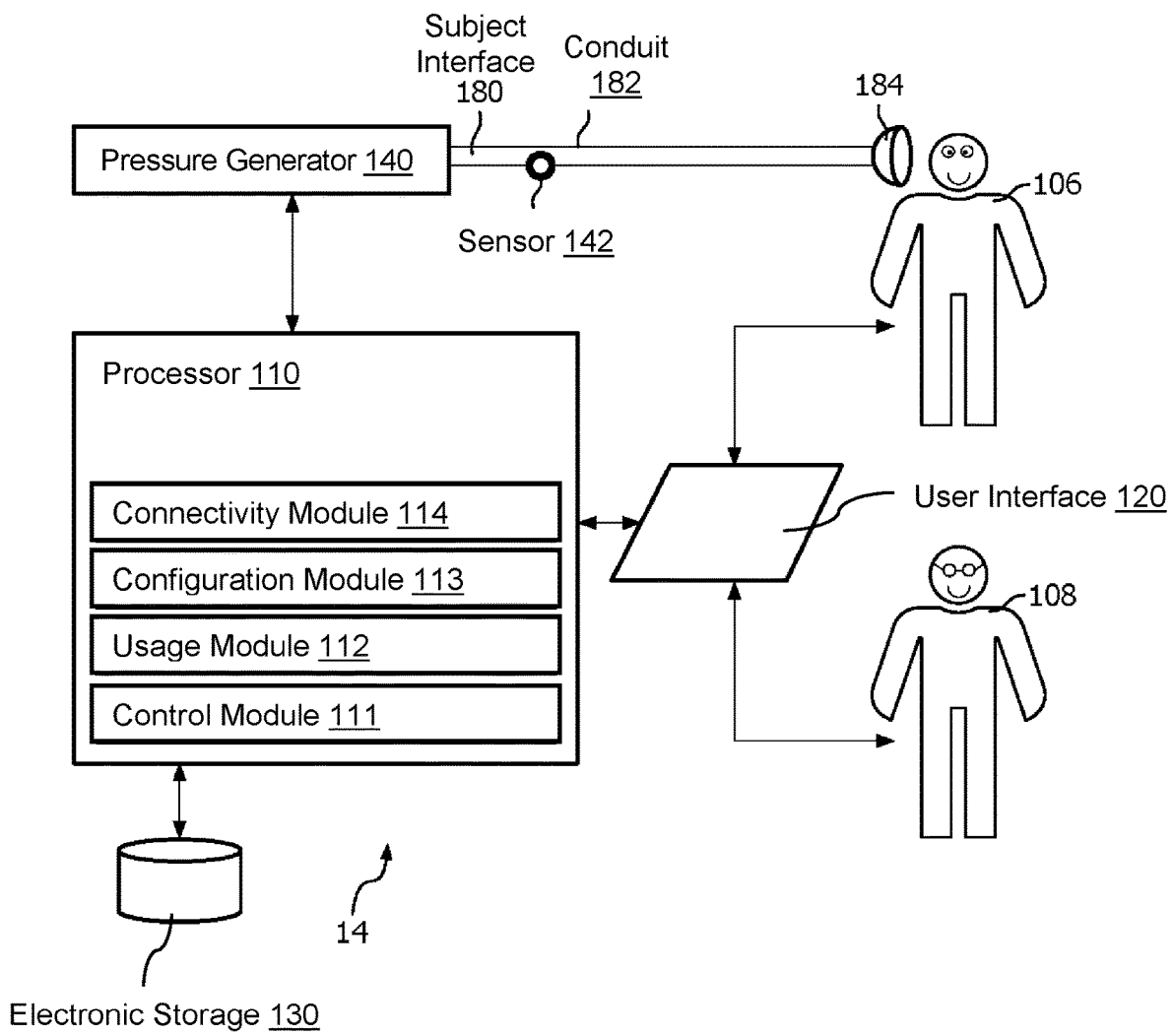
FIG. 2 schematically illustrates a respiratory therapy device capable of configuration in accordance with one or more embodiments.

FIG. 2 schematically illustrates a respiratory therapy device 14 that is capable of configuration in accordance with one or more embodiments. Respiratory therapy device 14 may comprise one or more of a pressure generator 140, a processor 110, a sensor 142, an electronic storage 130, a user interface 120, a subject interface 180, and/or other constituent components.

Pressure generator 140 is configured to provide a pressurized flow of breathable gas to the airway of subject 106, e.g. via subject interface 180. Subject 106 may or may not initiate one or more phases of respiration. Pressure support may be implemented as a higher and lower positive pressure of a (multi-level) respiratory therapy device 14. For example, to support inspiration, the pressure of the pressurized flow of breathable gas is adjusted to an Inspiratory Positive Air Pressure (IPAP). Similarly, to support expiration, the pressure of the pressurized flow of breathable gas is adjusted to an Expiratory Positive Air Pressure (EPAP). Other schemes for providing respiratory support (including bi-level pressure support, Average Volume Assured Pressure Support (AVAPS) mode; Proportional Assist Ventilation (PAV) mode; Auto Servo Ventilation (ASV) mode; Flow Based Gain Therapy (FBGT) mode; Loop Gain Therapy mode and/or other modes) through the delivery of the pressurized flow of breathable gas are contemplated. Note that a pressure level need not be constant throughout an entire phase of respiration.

Respiratory therapy device 14 may be configured such that one or more gas parameters of the pressurized flow of breathable gas are controlled in accordance with a therapeutic respiratory regimen for subject 106. The one or more gas parameters include one or more of flow, volume, retrograde volume, pressure, humidity, velocity, acceleration, (intentional) gas leak, and/or other parameters. Respiratory therapy device 14 may be configured to provide types of therapy including types of therapy where a subject performs inspiration and/or expiration of his own accord or where the device provides negative airway pressure.

A therapy "session" of using a respiratory therapy device 14 may be defined as a period of consecutive therapeutic usage of the respiratory therapy device 14, not to exceed 24 consecutive hours. If the respiratory therapy is used to treat sleeping disorders, such as sleep apnea, the related session length may correspond to the sleeping pattern of a subject. A typical session length may thus be at least 6-8 hours. In some modes of respiratory therapy, one or more pressure levels are adjusted on a relatively ongoing manner (e.g., each breath, every few breaths, every few seconds, etc.) during an individual therapy session to titrate the therapy. In other modes of therapy, adjustments may be made only between sessions rather than during sessions.

A pressurized flow of breathable gas is delivered from pressure generator 140 to or near the airway of subject 106 by a subject interface 180. Subject interface 180 includes a conduit 182, a subject interface appliance 184, and/or other components. Conduit 182 may be a flexible length of hose, or other conduit, that places subject interface appliance 184 in fluid communication with pressure generator 140. Conduit 182 forms a flow path through which the pressurized flow of breathable gas is communicated between subject interface appliance 184 and pressure generator 140.

Subject interface appliance 184 is configured to deliver the pressurized flow of breathable gas to the airway of subject 106. As such, subject interface appliance 184 may include any appliance suitable for this function. In certain embodiments, pressure generator 140 is a dedicated ventilation device and subject interface appliance 184 is configured to be removably coupled with another interface appliance being used to deliver respiratory therapy to subject 106. For example, subject interface appliance 184 is configured to engage with and/or be inserted into an endotracheal tube, a tracheotomy portal, and/or other interface appliances. In certain embodiments, subject interface appliance 184 is configured to engage the airway of subject 106 without an intervening appliance. In this embodiment, subject interface appliance 184 includes one or more of an endotracheal tube, a nasal cannula, a tracheotomy tube, a nasal mask, a nasal/oral mask, a full face mask, a total face mask, a partial rebreathing mask, or other interface appliances that communicate a flow of gas with an airway of a subject. The present disclosure is not limited to these examples, and contemplates delivery of the pressurized flow of breathable gas to subject 106 using any subject interface.

Respiratory therapy device 14 may include electronic storage 130 comprising electronic storage media that electronically stores information. The electronic storage media of electronic storage 130 includes one or both of system storage that is provided integrally (i.e., substantially non-removable) with respiratory therapy device 14 and/or removable storage that is removably connectable to respiratory therapy device 14 via, for example, a port (e.g., a USB port, a FireWire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media.

Electronic storage 130 stores software algorithms, information determined by processor 110, information received via user interface 120, and/or other information that enables respiratory therapy device 14 to function properly. For example, electronic storage 130 may record or store timing information (including duration of inhalation phases and exhalation phases as well as transitional moments), one or more (breathing) parameters and/or other parameters (as discussed elsewhere herein), pressure levels, information indicating whether the subject adequately complied with a prescribed respiratory therapy regimen, information indicating whether a respiratory event (including Cheyne-Stokes respiration, central sleep apnea, obstructive sleep apnea, hypopnea, snoring, hyperventilation, and/or other respiratory events) occurred, and/or other information. Electronic storage 130 may be a separate component within respiratory therapy device 14, or electronic storage 130 may be provided integrally with one or more other components of respiratory therapy device 14 (e.g., processor 110).

Respiratory therapy device 14 may include user interface 120 configured to provide an interface between respiratory therapy device 14 and a user (e.g., user 108, subject 106, a caregiver, a therapy decision-maker, etc.) through which the user can provide information to and receive information from respiratory therapy device 14. This enables data, results, and/or instructions and any other communicable items, collectively referred to as "information," to be communicated between the user and respiratory therapy device 14. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information is e.g. provided to subject 106 by user interface 120 in the form of auditory signals, visual signals, tactile signals, and/or other sensory signals.

By way of non-limiting example, in certain embodiments, user interface 120 includes a radiation source capable of emitting light. The radiation source includes one or more of an LED, a light bulb, a display screen, and/or other sources. User interface 120 controls the radiation source to emit light in a manner that conveys to subject 106 information related to breathing and/or the pressurized flow of breathable gas. Note that the subject and the user of respiratory therapy device 14 may be the same person.

It is to be understood that other communication techniques, either hard-wired or wireless, are also contemplated herein as user interface 120. For example, in one embodiment, user interface 120 is integrated with a removable storage interface provided by electronic storage 130. In this example, information is loaded into respiratory therapy device 14 from removable storage (e.g., a smart card, a flash drive, a removable disk, etc.) that enables the user(s) to customize the implementation of respiratory therapy device 14. Other exemplary input devices and techniques adapted for use with respiratory therapy device 14 as user interface 120 include, but are not limited to, an RS-232 port, RF link, an IR link, modem (telephone, cable, Ethernet, internet or other). In short, any technique for communicating information with respiratory therapy device 14 is contemplated as user interface 120.

Respiratory therapy device 14 may include sensor 142 configured to generate one or more output signals conveying measurements related to respiratory parameters, including one or more of flow, pressure, humidity, velocity, acceleration, and/or other respiratory parameters. Output signals may convey measurements related to respiratory parameters. Based on these respiratory parameter, respiratory therapy device 14 (and/or any constituent components thereof) may be configured to determine one or more breathing parameters, including (tidal) volume, retrograde volume, respiratory rate, breathing period, inhalation time or period, exhalation time or period, peak flow, flow rate, respiration flow curve shape, transition time from inhalation to exhalation and/or vice versa, transition time from peak inhalation flow rate to peak exhalation flow rate and/or vice versa, respiration pressure curve shape, (intentional) gas leak, and/or other breathing parameters. Sensor 142 may be in fluid communication with conduit 182 and/or subject interface appliance 184.

The illustration of sensor 142 as including a single member in FIG. 2 is not intended to be limiting. In certain embodiments sensor 142 includes a plurality of sensors operating as described above by generating output signals conveying information related to parameters associated with the gas breathed by subject 106 and/or the delivery of the gas to subject 106. For example, a breathing parameter may be related to a mechanical unit of measurement of a component of respiratory therapy device 14 such as rotor speed, motor speed, blower speed, fan speed, or a related measurement that serves as a proxy for any of the previously listed breathing parameters through a previously known/calibrated mathematical relationship. Resulting signals or information from sensor 142 may be transmitted to processor 110, user interface 120, electronic storage 130, and/or other components of respiratory therapy device 14. This transmission can be wired and/or wireless.

Processor 110 is configured to provide information processing capabilities in respiratory therapy device 14. As such, processor 110 includes one or more of a digital processor, an analog processor, a digital circuit designed to process information, an analog circuit designed to process information, a state machine, and/or other mechanisms for electronically processing information. Although processor 110 is shown in FIG. 2 as a single entity, this is for illustrative purposes only. In some implementations, processor 110 includes a plurality of processing units.

As is shown in FIG. 2, processor 110 is configured to execute one or more computer program modules. The one or more computer program modules include one or more of a control module 111, a usage module 112, a configuration module 113, a connectivity module 114, and/or other modules. Processor 110 may be configured to execute modules 111, 112, 113, and/or 114 by software; hardware; firmware; some combination of software, hardware, and/or firmware; and/or other mechanisms for configuring processing capabilities on processor 110.

It should be appreciated that although modules 111, 112, 113, and 114 are illustrated in FIG. 2 as being co-located within a single processing unit, in implementations in which processor 110 includes multiple processing units, one or more of modules 111, 112, 113, and/or 114 may be located remotely from the other modules. The description of the functionality provided by the different modules 111, 112, 113, and/or 114 described below is for illustrative purposes, and is not intended to be limiting, as any of modules 111, 112, 113, and/or 114 may provide more or less functionality than is described. For example, one or more of modules 111, 112, 113, and/or 114 may be eliminated, and some or all of its functionality may be provided by other ones of modules 111, 112, 113, and/or 114. Note that processor 110 may be configured to execute one or more additional modules that may perform some or all of the functionality attributed below to one of modules 111, 112, 113, and/or 114.

Control module 111 is configured to control pressure generator 140 in the provision of adjusting pressure levels for respiratory therapy device 14, to provide the pressurized flow of breathable gas at inhalation pressure levels during inhalation phases, and at exhalation pressure levels during exhalation phases.

Usage module 112 is configured to monitor, track, and/or gather therapeutic usage information for a given user associated with respiratory therapy device 14. Usage information may include one or more of a therapy starting date, user experience level, an average duration of daily usage, a usage pattern, metrics indicating quality of therapy and/or quality of sleep, level of compliance with a therapy regimen, therapeutic device characteristics (e.g. mask type or operational settings), derived usage characteristics, user-stated usage characteristics, and/or other usage information. User-stated usage characteristics may include issues or problems the user is experiencing while undergoing therapy, and/or other user-stated usage characteristics. Derived usage characteristics may include low and/or irregular usage (as detected e.g. through analysis of usage reports), decreasing usage, excessive mask leak, and/or other derived usage characteristics.

Configuration module 113 is configured to adjust mode settings and other operational parameters for respiratory therapy device 14. For example, configuration module 113 may have one set of operational parameters for a first therapy mode, and a second set of operational parameters for a second, third, or subsequent therapy mode. The first therapy mode may be an initial, default, or original therapy mode. For example, a new user (e.g. newly registered user of system 10) using respiratory therapy device 14 may start respiratory therapy by default in a particular therapy mode, such as a CPAP therapy mode.

Connectivity module 114 is configured to enable interaction between respiratory therapy device 14 and system 10. Connectivity module 114 may transmit information, such as usage information, from usage module 112 to system 10 (and/or data gathering module 22 shown in FIG. 1). Connectivity module 114 may receive commands issued and/or transmitted by system 10 (and/or device configuration module 24 shown in FIG. 1). For example, such a command may contain instructions to change a mode parameter. Connectivity module 114 may cause configuration module 113 to carry out the instructions contained in the command.

Figure 4:
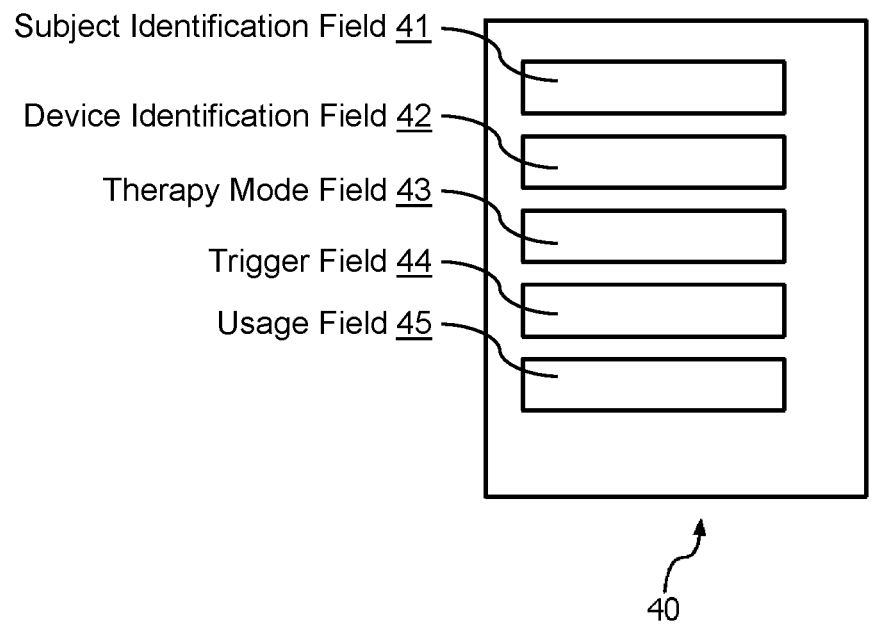
FIG. 4 illustrates an exemplary embodiment of a user interface within a respiratory therapy device capable of configuration in accordance with one or more embodiments.

FIG. 4 illustrates an exemplary embodiment of a user interface 40 within respiratory therapy device 14, capable of configuration in accordance with one or more embodiments. User interface 40 may include one or more fields configured to receive entry and/or selection of information pertaining to operational parameters and/or conditions of respiratory therapy device 14. Field 41 may be a subject identification field configured to present an identifier of the current subject associated with a given respiratory therapy device 14. Field 42 may be a device identification field configured to present an identifier of the given respiratory therapy device 14. Field 43 may be a therapy mode/activate field configured to present the current therapy mode (and/or any of the parameters/settings associated with the current therapy mode) for a given respiratory therapy device 14.

Responsive to a second therapy mode being unlocked through provider interface mode 27, field 43 may present a selectable acceptance field, e.g., labeled with an identifier and/or representation of the unlocked second therapy mode. Selection of the selectable acceptance field activates the unlocked second therapy mode for the given respiratory therapy device 14 (either indefinitely or for a trial period). Field 44 may be a message field configured to present information from a care provider, e.g. pertaining to the current respiratory therapy. Field 45 may be a usage field configured to present usage information to a user. For example, field 45 may present the average number of hours of nightly usage of a given respiratory therapy device 14 or information pertaining to the determined, measured, estimated, and/or approximated effectiveness of the current therapy mode. The same process make take place responsive to a third or subsequent therapy mode being unlocked.

Figure 5:
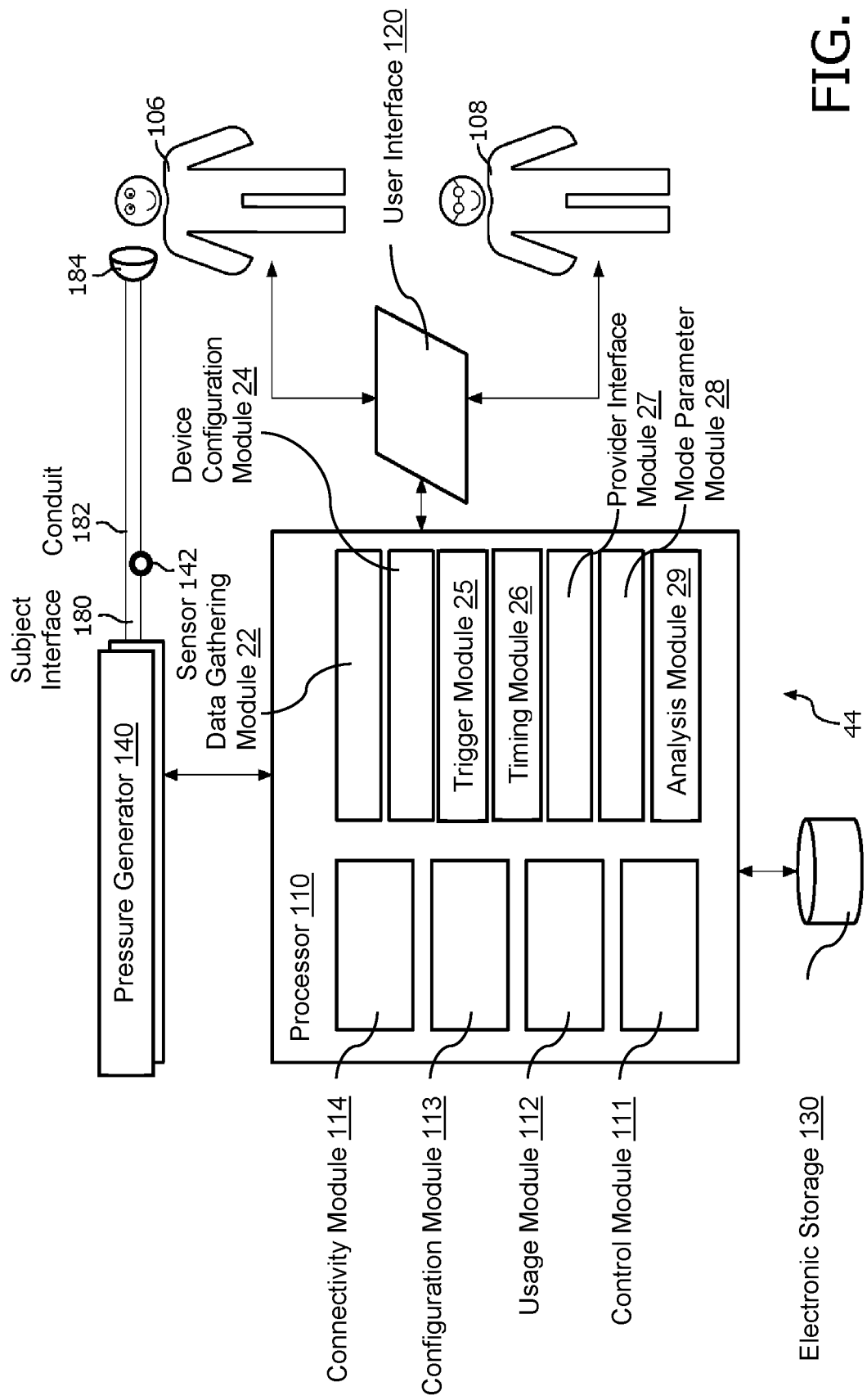
FIG. 5 schematically illustrates a respiratory therapy device capable of configuration in accordance with one or more embodiments.

FIG. 5 schematically illustrates a respiratory therapy device 44 that is capable of configuration in accordance with one or more embodiments. Respiratory therapy device 44 may comprise one or more of pressure generator 140, processor 110, sensor 142, electronic storage 130, user interface 120, subject interface 180, and/or other constituent components. Pressure generator 140, processor 110, sensor 142, electronic storage 130, user interface 120, and subject interface 180 perform the same or similar functionality as their respective counterparts in FIG. 2, described above. Respiratory therapy device 44 includes one or more of control module 111, usage module 112, configuration module 113, and/or connectivity module 114, which perform the same or similar functionality as their respective counterparts in FIG. 2, described above. Respiratory therapy device 44 may further include one or more of data gathering module 22, device configuration module 24, trigger module 25, timing module 26, provider interface module 27, mode parameter module 28, and analysis module 29, which perform the same or similar functionality as their respective counterparts in FIG. 1, described above. Respiratory therapy device 44 does not require a connection to one or more networks to perform the functionality of configuring therapy modes.

Figure 6:
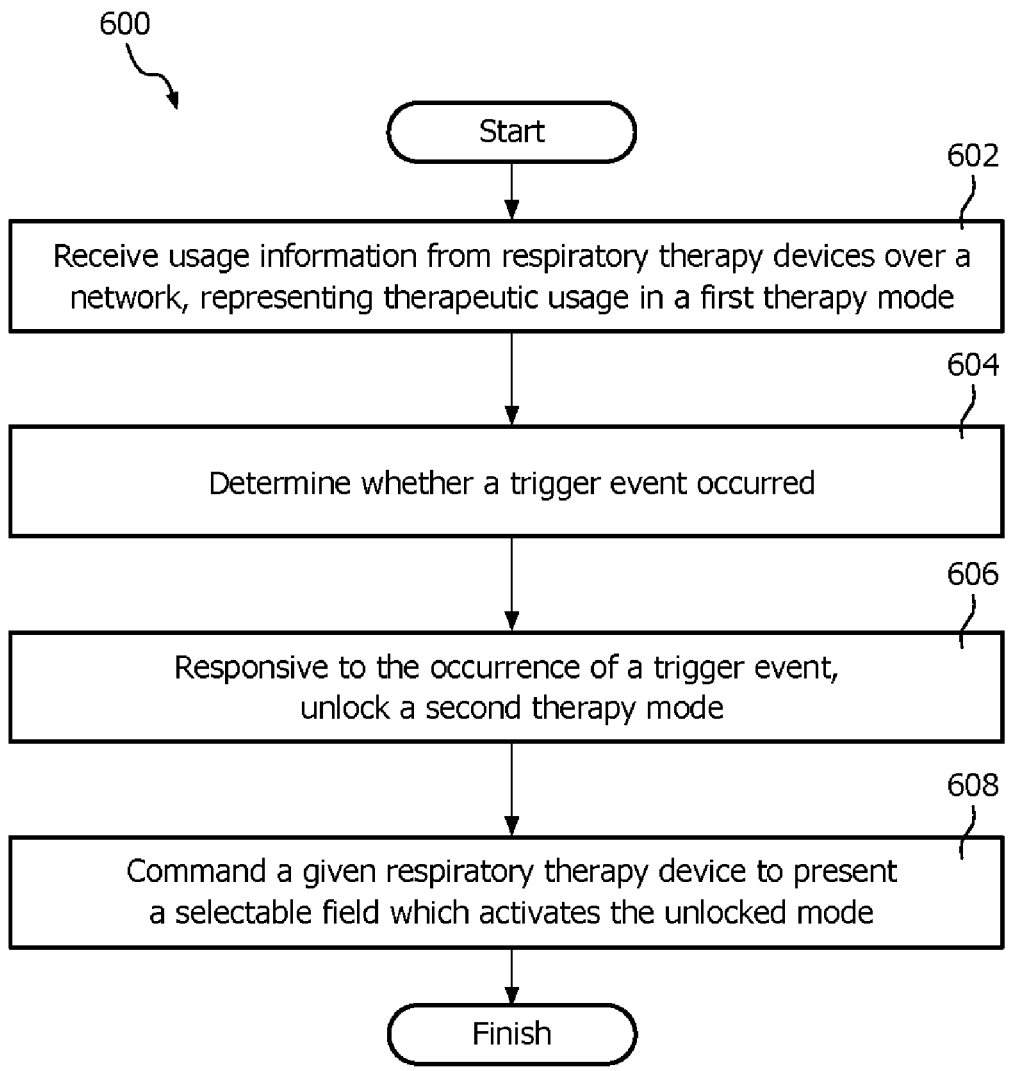
FIG. 6 illustrates a method for configuring respiratory therapy modes for users of respiratory therapy devices.

FIG. 6 illustrates a method 600 of configuring respiratory therapy modes for users of respiratory therapy devices. The operations of method 600 presented below are intended to be illustrative. In some embodiments, method 600 may be accomplished with one or more additional operations not described, and/or without one or more of the operations discussed. Additionally, the order in which the operations of method 600 are illustrated in FIG. 6 and described below is not intended to be limiting.

In some embodiments, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, usage information is received from a respiratory therapy device, wherein the usage information represents therapeutic usage of the device in a first therapy mode. In some implementations, operation 602 may be performed by a data gathering module similar to or substantially the same as data gathering module 22 (shown in FIG. 1 and described above).

At an operation 604, the occurrence of a trigger event pertaining to a given respiratory therapy device is determined. In some implementations, operation 604 may be performed by a trigger module similar to or substantially the same as trigger module 25 (shown in FIG. 1 and described above).

At an operation 606, a second therapy mode is unlocked, responsive to the occurrence of a trigger event. In some implementations, operation 606 may be performed by a provider interface module similar to or substantially the same as provider interface module 27 (shown in FIG. 1 and described above).

At an operation 608, the respiratory therapy device is commanded to present a selectable field. Selection of the field activates the second therapy mode for the given respiratory therapy device. In some implementations, operation 608 may be performed by a device configuration module similar to or substantially the same as device configuration module 24 (shown in FIG. 1 and described above). A similar process is followed to active a third therapy mode for the given respiratory device.

Figure 7:
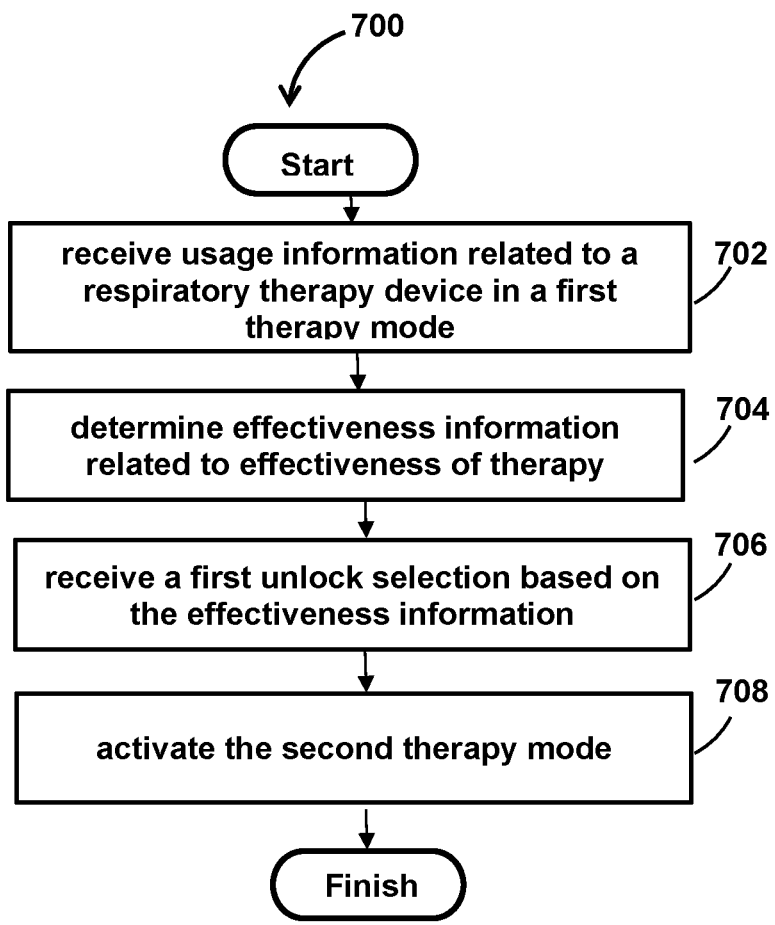
FIG. 7 illustrates a method for configuring respiratory therapy modes for users of respiratory therapy devices.
Figure 8:
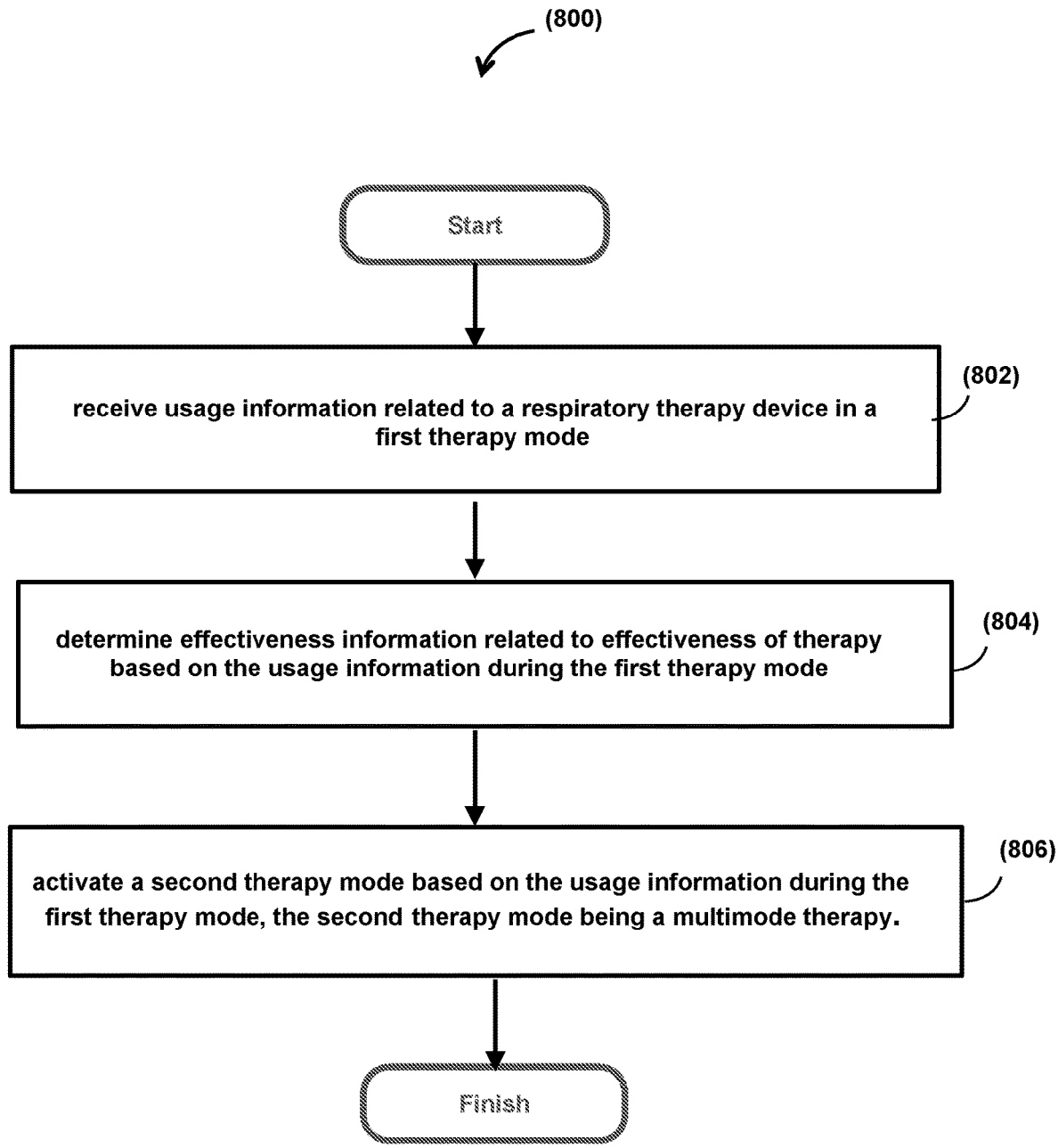
FIG. 8 illustrates a method for configuring respiratory therapy modes for users of respiratory therapy devices.

FIG. 7 illustrates a method 700 of configuring respiratory therapy modes for users of respiratory therapy devices. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, usage information is received from a respiratory therapy device, wherein the usage information represents therapeutic usage of the device in a first therapy mode. In some implementations, operation 702 may be performed by a data gathering module similar to or substantially the same as data gathering module 22 (shown in FIG. 1 and described above).

At an operation 704, effectiveness information related to effectiveness of therapy is determined based on the usage information during the first therapy mode. In some implementations, operation 704 may be performed by an analysis module similar to or substantially the same as analysis module 29 (shown in FIG. 1 and described above).

At an operation 706, a first unlock selection is received based on the determined effectiveness information. In some embodiments, the first unlock selection is received while the respiratory therapy device is operating in the first therapy mode. In some embodiments, the first unlock selection indicates that a second therapy mode for the respiratory therapy device should be unlocked. In some embodiments, the second therapy mode is different than the first therapy mode. In some embodiments, the second therapy mode is not available for use on the respiratory therapy device prior to reception of the first unlock selection. In some implementations, operation 706 may be performed by a provider interface module similar to or substantially the same as provider interface module 27 (shown in FIG. 1 and described above).

In some embodiments, method 800 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 800 in response to instructions stored electronically on an electronic storage medium. The one or more processing devices may include one or more devices configured through hardware, firmware, and/or software to be specifically designed for execution of one or more of the operations of method 800.

At an operation 802, usage information is received from a respiratory therapy device in a first therapy mode. In some implementations, operation 802 may be performed by processor(s) 20 (shown in FIG. 1 and described above).

At an operation 804, effectiveness information related to effectiveness of therapy is determined based on the usage information during the first therapy mode. In some implementations, operation 804 may be performed by processor(s) 20 (shown in FIG. 1 and described above).

At an operation 806, a second therapy mode is activated based on the usage information during the first therapy mode, the second therapy mode being a multimode therapy. In some implementations, operation 806 may be performed by processor(s) 20 (shown in FIG. 1 and described above).

At an operation 708, the second therapy mode for the respiratory therapy device is activated. In some embodiments, the second therapy mode is activated responsive to reception of the first unlock selection by the provider interface module. In some implementations, operation 708 may be performed by a device configuration module similar to or substantially the same as device configuration module 24 (shown in FIG. 1 and described above). A similar process is followed to active a third or subsequent therapy modes for the given respiratory device.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the embodiments have been described in detail for the purpose of illustration based on what is currently considered to be most practical and preferred, it is to be understood that such detail is solely for that purpose and that the disclosure is not limited to these embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system to configure respiratory therapy modes for users of respiratory therapy devices, the system comprising:
   one or more processors configured to execute computer program modules, the computer program modules comprising:
      a data gathering module configured to receive usage information related to a respiratory therapy device in a first therapy mode, wherein the usage information received from the respiratory therapy device represents therapeutic usage of the respiratory therapy device during the first therapy mode;
      an analysis module configured to determine effectiveness information related to effectiveness of therapy based on the usage information during the first therapy mode;
      a provider interface module configured to receive a first unlock selection based on the determined effectiveness information, the first unlock selection being received while the respiratory therapy device is operating in the first therapy mode, the first unlock selection indicating that a second therapy mode for the respiratory therapy device should be unlocked, wherein
   the second therapy mode is different than the first therapy mode, and
   the second therapy mode is not available for use on the respiratory therapy device prior to reception of the first unlock selection; and
      a device configuration module configured such that, responsive to reception of the first unlock selection by the provider interface module, the device configuration module activates the second therapy mode for the respiratory therapy device.

2. The system of claim 1, wherein the device configuration module is further configured such that, responsive to reception of a second unlock selection by the provider interface module, the device configuration module activates a third therapy mode for the respiratory therapy device.

3. The system of claim 1, wherein the device configuration module is further configured such that, responsive to reception of the first or the second unlock selection, the device configuration module causes the respiratory therapy device to activate a selectable acceptance field, wherein user selection of the selectable acceptance field indicates acceptance of the second or the third therapy mode, respectively, and wherein activation of the second or the third therapy mode for the respiratory therapy device is further responsive to user selection of the selectable acceptance field.

4. The system of claim 1, further comprising a trigger module configured to determine whether a trigger event occurred pertaining to the respiratory therapy device based on the determination of the effectiveness information by the analysis module.

5. The system of claim 4, wherein the trigger event is based on the usage information.

6. The system of claim 1, wherein the unlocked second or the third therapy mode includes a multimode therapy.

7. The system of claim 1, wherein the usage information received from the respiratory therapy device comprises an index related to effectiveness of therapy provided by the respiratory therapy device.

8. The system of claim 1, wherein deactivation of the second therapy mode comprises activation of the third therapy mode, and wherein the second therapy mode is not available for use on the respiratory therapy device after deactivation of the second therapy mode.

9. A method to configure respiratory therapy modes for users of respiratory therapy devices, the method comprising:
   receiving usage information related to a respiratory therapy device in a first therapy mode, wherein the received usage information represents therapeutic usage of the respiratory therapy device during the first therapy mode;
   determining effectiveness information related to effectiveness of therapy based on the usage information during the first therapy mode;
   receiving a first unlock selection based on the effectiveness information, the first unlock selection being received while the respiratory therapy device is operating in the first therapy mode, the first unlock selection indicating that a second therapy mode for the respiratory therapy device should be unlocked, wherein
      the second therapy mode is different than the first therapy mode, and
      the second therapy mode is not available for use on the respiratory therapy device prior to reception of the first unlock selection; and
   responsive to reception of the first unlock selection, activating the second therapy mode for the respiratory therapy device.

10. The method of claim 9, further comprising activating a third therapy mode for the respiratory therapy device responsive to reception of a second unlock selection by the provider interface module.

11. The method of claim 9, wherein activating the second therapy mode includes:
   causing the respiratory therapy device to activate a selectable acceptance field, wherein user selection of the selectable acceptance field indicates acceptance of the second therapy mode, and
   responsive to user selection of the selectable acceptance field, activating the second therapy mode.

12. The method of claim 9, further comprising determining whether a trigger event pertaining to the respiratory therapy device occurred, wherein reception of the first or the second unlock selection is responsive to an occurrence of the trigger event.

13. The method of claim 12, wherein the trigger event is based on the usage information from the respiratory therapy device.

14. The method of claim 9, wherein the second or the third therapy mode includes multimode therapy.

15. The method of claim 9, wherein the usage information received from the respiratory therapy device comprises an index related to effectiveness of therapy provided by the respiratory therapy device.

16. A system for configuring respiratory therapy modes for users of respiratory therapy devices, the system comprising:
means for receiving usage information related to a respiratory therapy device in a first therapy mode, wherein the received usage information represents therapeutic usage of the respiratory therapy device during the first therapy mode;
means for determining effectiveness information related to effectiveness of therapy based on the usage information during the first therapy mode;
means for receiving a first unlock selection based on the effectiveness information, the first unlock selection being received while the respiratory therapy device is operating in the first therapy mode, the first unlock selection indicating that a second therapy mode for the respiratory therapy device should be unlocked, wherein the second therapy mode is different than the first therapy mode, and
the second therapy mode is not available for use on the respiratory therapy device prior to reception of the first unlock selection; and
means for activating the second therapy mode for the respiratory therapy device, responsive to reception of the first unlock selection.

17. The system of claim 16, comprising means for activating a third therapy mode for the respiratory therapy device responsive to reception of a second unlock selection by the provider interface module.

18. The system of claim 16, wherein the means for activating the second therapy mode includes: means for causing the respiratory therapy device to activate a selectable acceptance field, wherein user selection of the selectable acceptance field indicates acceptance of the second therapy mode, and means for activating the second therapy mode, responsive to user selection of the selectable acceptance field.

19. The system of claim 16, further comprising means for determining whether a trigger event pertaining to the respiratory therapy device occurred, wherein operation of the means for receiving the first or the second unlock selection is responsive to an occurrence of the trigger event.

20. The system of claim 19, wherein the trigger event is based on the usage information from the respiratory therapy device.

21. The system of claim 16, wherein the second or the third therapy mode includes multimode therapy.

22. The system of claim 16, wherein the usage information comprises an index related to effectiveness of therapy provided by the respiratory therapy device.

23. A non-transitory computer-readable medium storing instructions that, when executed by a computer, cause it to:
receive usage information related to a respiratory therapy device in a first therapy mode, wherein the received usage information represents therapeutic usage of the respiratory therapy device during the first therapy mode;
determine effectiveness information related to effectiveness of therapy based on the usage information during the first therapy mode;
receive a first unlock selection based on the effectiveness information, the first unlock selection being received while the respiratory therapy device is operating in the first therapy mode, the first unlock selection indicating that a second therapy mode for the respiratory therapy device should be unlocked, wherein the second therapy mode is not available to use on the respiratory therapy device prior to reception of the first unlock selection, and
activate, in response to reception of the first unlock selection, the second therapy mode, the second therapy mode being a multimode therapy.

24. The non-transitory computer-readable medium of claim 23, wherein the multimode therapy is a combination of one or more fixed modality positive airway pressure (PAP) therapy modes, combined to address instability of the subject caused by the first therapy mode, wherein a fixed modality PAP therapy mode is configured to address a fixed clinical condition of the subject.

25. The non-transitory computer-readable medium of claim 24 wherein the one or more fixed modality (PAP) therapy modes comprises Average Volume Assured Pressure Support (AVAPS) mode, Proportional Assist Ventilation (PAV) mode, Auto Servo Ventilation (ASV) mode, Flow Based Gain Therapy (FBGT) mode, and/or Loop Gain Therapy mode.

26. The non-transitory computer-readable medium of claim 23, wherein determining effectiveness of therapy during the first therapy mode includes determining stability of the subject during the first therapy mode.

27. A method to configure respiratory therapy modes for users of respiratory therapy devices with a system comprising one or more physical computer processors, the method comprising:
receiving, with the one or more physical computer processors, usage information related to a respiratory therapy device in a first therapy mode, wherein the received usage information represents therapeutic usage of the respiratory therapy device during the first therapy mode;
determining, with the one or more physical computer processors, effectiveness information related to effectiveness of therapy based on the usage information during the first therapy mode;
receiving, with the one or more physical computer processors, a first unlock selection based on the effectiveness information, the first unlock selection being received while the respiratory therapy device is operating in the first therapy mode, the first unlock selection indicating that a second therapy mode for the respiratory therapy device should be unlocked, wherein the second therapy mode is not available to use on the respiratory therapy device prior to reception of the first unlock selection, and
activating, with the one or more physical computer processors, in response to reception of the first unlock selection, the second therapy mode, the second therapy mode being a multimode therapy.

28. The method of claim 27, wherein the multimode therapy is a combination of one or more fixed modality positive airway pressure (PAP) therapy modes, combined to address instability of the subject caused by the first therapy mode, wherein a fixed modality PAP therapy mode is configured to address a fixed clinical condition of the subject.

29. The method of claim 28, wherein the one or more fixed modality (PAP) therapy modes comprises Average Volume Assured Pressure Support (AVAPS) mode, Proportional Assist Ventilation (PAV) mode, Auto Servo Ventilation (ASV) mode, Flow Based Gain Therapy (FBGT) mode, and/or Loop Gain Therapy mode.

30. The method of claim 27, wherein determining effectiveness of therapy during the first therapy mode includes determining stability of the subject during the first therapy mode.

31. A system for configuring respiratory therapy modes for users of respiratory therapy devices, the system comprising:
means for receiving usage information related to a respiratory therapy device in a first therapy mode, wherein the received usage information represents therapeutic usage of the respiratory therapy device during the first therapy mode;
means for determining effectiveness information related to effectiveness of therapy based on the usage information during the first therapy mode;
receive a first unlock selection based on the effectiveness information, the first unlock selection being received while the respiratory therapy device is operating in the first therapy mode, the first unlock selection indicating that a second therapy mode for the respiratory therapy device should be unlocked, wherein the second therapy mode is not available to use on the respiratory therapy device prior to reception of the first unlock selection, and
means for activating, in response to reception of the first unlock selection, the second therapy mode, the second therapy mode being a multimode therapy.

32. The system of claim 31, wherein the multimode therapy is a combination of one or more fixed modality positive airway pressure (PAP) therapy modes, combined to address instability of the subject caused by the first therapy mode, wherein a fixed modality PAP therapy mode is configured to address a fixed clinical condition of the subject.

33. The system of claim 32, wherein the one or more fixed modality (PAP) therapy modes comprises Average Volume Assured Pressure Support (AVAPS) mode, Proportional Assist Ventilation (PAV) mode, Auto Servo Ventilation (ASV) mode, Flow Based Gain Therapy (FBGT) mode, and/or Loop Gain Therapy mode.

34. The system of claim 31, wherein determining effectiveness of therapy during the first therapy mode includes determining stability of the subject during the first therapy mode.

* * * * *